(12) United States Patent
Boutillette et al.

(10) Patent No.: US 7,717,865 B2
(45) Date of Patent: May 18, 2010

(54) SIDE LOADING WIRE TORQUING DEVICE

(75) Inventors: Michael P. Boutillette, Waltham, MA (US); Dmitri Menn, Ashland, MA (US); Eric Welch, Miramar, FL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 150 days.

(21) Appl. No.: 10/675,223

(22) Filed: Sep. 30, 2003

(65) Prior Publication Data
US 2005/0070820 A1   Mar. 31, 2005

(51) Int. Cl.
*A61B 5/00* (2006.01)
*A61M 5/178* (2006.01)
*A61M 25/00* (2006.01)

(52) U.S. Cl. ..................... 600/585; 604/159; 604/528

(58) Field of Classification Search ............... 600/585; 604/27, 93.01, 95.03, 95.04, 164.01, 164.13, 604/165.01, 165.03, 165.04, 264, 159; 606/103, 606/108; 226/127–128, 158; D24/133; 24/115 M, 24/136 R
See application file for complete search history.

(56) References Cited

U.S. PATENT DOCUMENTS

| | | | |
|---|---|---|---|
| 4,057,186 A * | 11/1977 | Hedger | ............... 226/127 |
| 4,425,919 A | 1/1984 | Alston, Jr. et al. | |
| 4,615,472 A | 10/1986 | Nash | |
| 4,643,720 A | 2/1987 | Lanciano | |
| 4,664,113 A | 5/1987 | Frisbie et al. | |
| 4,726,369 A | 2/1988 | Mar | |
| 4,799,496 A * | 1/1989 | Hargreaves et al. | ......... 600/585 |
| 4,817,613 A | 4/1989 | Jaraczewski et al. | |
| 4,829,999 A | 5/1989 | Auth | |
| 4,841,976 A | 6/1989 | Packard et al. | |
| 4,858,810 A | 8/1989 | Intlekofer et al. | |
| 4,957,117 A | 9/1990 | Wysham | |
| 4,998,916 A | 3/1991 | Hammerslag et al. | |
| 5,055,109 A | 10/1991 | Gould et al. | |
| 5,137,517 A | 8/1992 | Loney et al. | |
| 5,161,534 A | 11/1992 | Berthiaume | |
| 5,163,911 A | 11/1992 | Sirimanne et al. | |
| 5,178,159 A | 1/1993 | Christian | |
| 5,195,968 A | 3/1993 | Lundquist et al. | |
| 5,203,772 A | 4/1993 | Hammerslag et al. | |
| 5,217,435 A | 6/1993 | Kring | |
| 5,219,332 A | 6/1993 | Nelson et al. | |

(Continued)

*Primary Examiner*—Max Hindenburg
*Assistant Examiner*—H. Q. Nguyen
(74) *Attorney, Agent, or Firm*—Crompton, Seager & Tufte, LLC

(57) ABSTRACT

A side loading, wire torquing device includes a body portion having a channel in which a wire is fitted. In one embodiment, a slider is movable along the channel to secure the wire between the slider and the fixed surface in the channel such that rotation of the torquing device rotates the wire therein. In another embodiment of the invention, the torquing device includes a bottom and top section folded over a wire. In another embodiment, the channels impart a bend to the wire to increase the effective torque that can be applied to the wire by rotating the device. In yet another embodiment, the torquing device has a tapered shape and includes a ring that is slideable over the device to compress a wire in a channel. In all embodiments, the torquing device may include a clip to secure several looped coils of wire when not in use.

11 Claims, 6 Drawing Sheets

U.S. PATENT DOCUMENTS

| | | |
|---|---|---|
| 5,242,430 A | 9/1993 | Arenas et al. |
| 5,275,151 A | 1/1994 | Shockey et al. |
| 5,312,338 A | 5/1994 | Nelson et al. |
| 5,313,967 A | 5/1994 | Lieber et al. |
| 5,315,996 A | 5/1994 | Lundquist |
| 5,325,746 A | 7/1994 | Anderson |
| 5,325,868 A | 7/1994 | Kimmelstiel |
| 5,354,297 A | 10/1994 | Avitall |
| 5,364,352 A | 11/1994 | Cimino et al. |
| 5,392,778 A | 2/1995 | Horzewski |
| 5,423,331 A | 6/1995 | Wysham |
| 5,507,728 A | 4/1996 | Erskine |
| 5,558,101 A | 9/1996 | Brooks et al. |
| 5,562,619 A | 10/1996 | Mirarchi et al. |
| 5,662,606 A | 9/1997 | Cimino et al. |
| 5,690,616 A | 11/1997 | Mogg |
| 5,820,592 A | 10/1998 | Hammerslag |
| 5,846,229 A | 12/1998 | Berg |
| 5,851,189 A | 12/1998 | Forber |
| 5,873,864 A | 2/1999 | Luther et al. |
| 5,891,088 A | 4/1999 | Thompson et al. |
| 5,931,830 A | 8/1999 | Jacobsen et al. |
| 5,935,102 A * | 8/1999 | Bowden et al. .......... 604/95.04 |
| 5,944,690 A | 8/1999 | Falwell et al. |
| 6,030,349 A | 2/2000 | Wilson et al. |
| 6,033,414 A | 3/2000 | Tockman et al. |
| 6,059,484 A * | 5/2000 | Greive ........................ 403/305 |
| 6,059,739 A | 5/2000 | Baumann |
| 6,169,916 B1 | 1/2001 | West |
| 6,176,852 B1 | 1/2001 | Ischinger |
| 6,224,587 B1 | 5/2001 | Gibson |
| 6,246,914 B1 | 6/2001 | de la Rama et al. |
| 6,511,470 B1 | 1/2003 | Hamilton |
| 6,533,772 B1 * | 3/2003 | Sherts et al. .................. 606/1 |
| 2002/0068868 A1 | 6/2002 | Thompson et al. |
| 2002/0077590 A1 | 6/2002 | Ponzi et al. |
| 2002/0177789 A1 | 11/2002 | Ferry et al. |
| 2003/0036712 A1 | 2/2003 | Heh et al. |

* cited by examiner

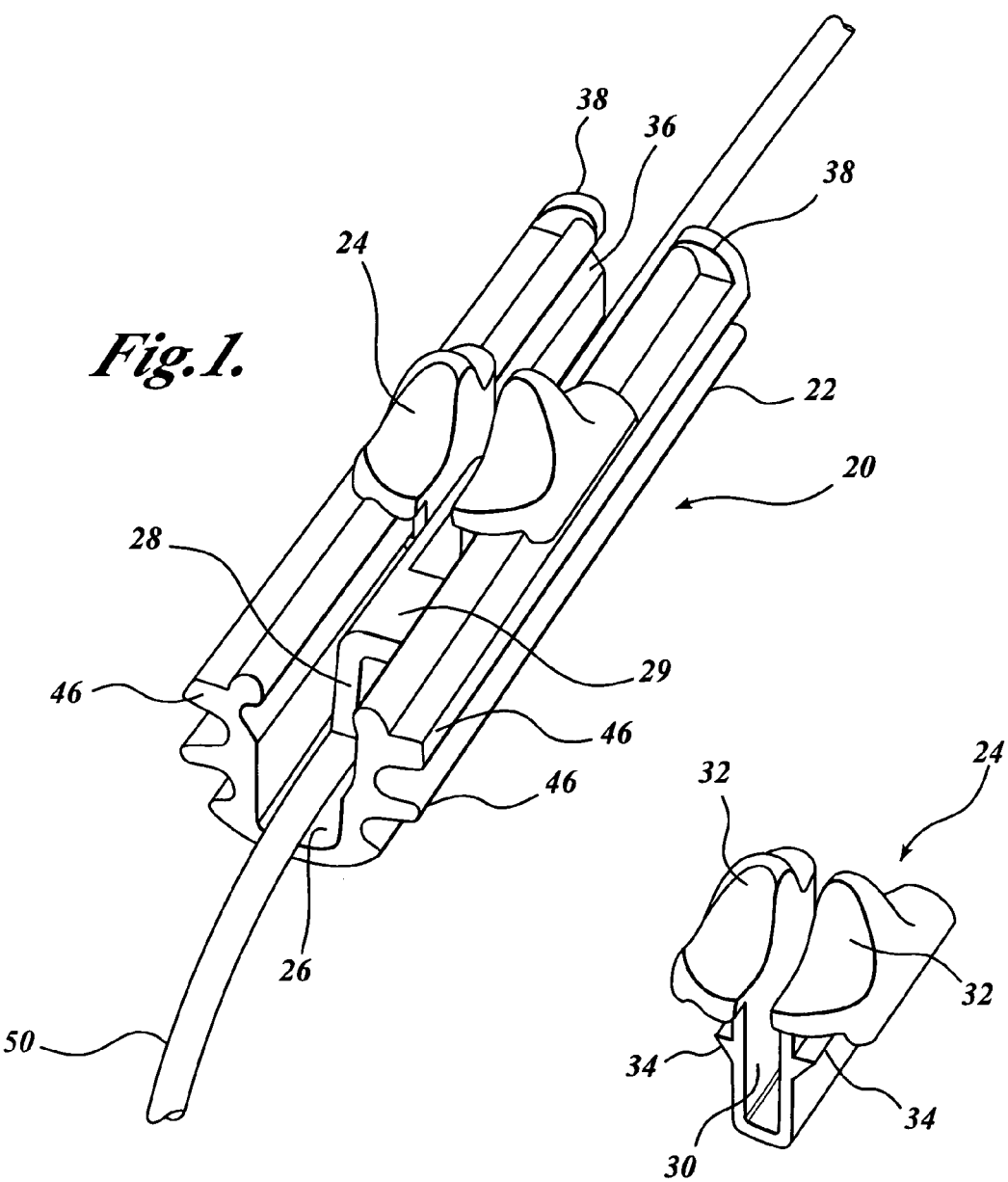
Fig.1.
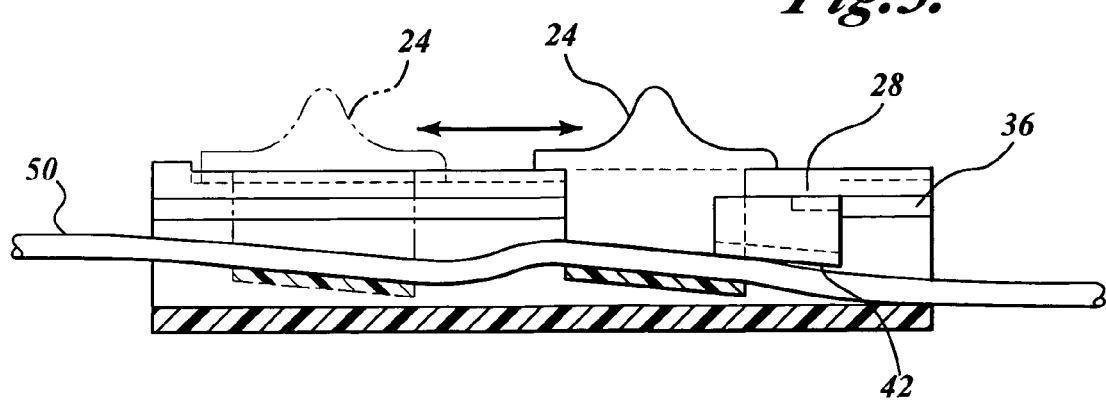
Fig.3.
Fig.2.

SIDE LOADING WIRE TORQUING DEVICE

FIELD OF THE INVENTION

The present invention relates to medical devices in general, and in particular to devices for applying torque to thin wires or cables.

BACKGROUND OF THE INVENTION

Many minimally invasive medical procedures require a guidewire to be inserted into a patient and one or more catheters or other medical devices to be advanced over the guidewire in order to perform a medical procedure, view body tissue or obtain a tissue sample. While performing a procedure, it is not uncommon that the physician wishes to change the orientation of the guidewire. This is particularly true if the guidewire has an angled tip and the physician is trying to direct the tip into a branch in a patient's vasculature. Because guidewires are long, thin wires, it is difficult to maintain an adequate purchase on a guidewire in order to impart torque to its distal end. Therefore, many physicians use a guidewire torquing device that clamps on to the wire in order to allow the physician to twist it.

Most guidewire torquing devices are advanced axially over the proximal end of the guidewire and include a pin vise or sliding locking mechanism that compresses the guidewire in order to secure it. Such torquing devices generally require two hands to operate and require the physician to load the torquing device over the entire proximal length of the guidewire. Other types of guidewire torquing devices are side loading, clip-like devices that grasp a guidewire in a channel. However, most clip-like side loading torquing devices do not maintain an adequate purchase on a wire to allow a user to impart torque to its distal end.

Given these problems, there is a need for a side loading wire torquing device that can be operated with a single hand and that can allow a user to impart torque to it. In addition, the device should be easy and inexpensive to manufacture.

SUMMARY OF THE INVENTION

A wire torquing device in accordance with one embodiment of the invention includes a body portion having an open side channel into which a wire can be fitted. A slider that is movable along the channel secures a wire between the slider and a fixed surface that is disposed within the channel. With the wire secured, torque can be applied to the wire by rotating the body portion.

In another embodiment of the invention, the wire torquing device has a clam shell structure with a top and bottom section that are folded around a wire. A channel within the top and bottom sections receives a wire that is secured when the top section is folded over the bottom section. The channel in the top and bottom sections include a wire bending mechanism to impart one or more curves to the wire in order to aid in torquing the wire as the body portion is rotated.

In yet another embodiment, the wire torquing device includes a channel and a tapered outer surface with one end having a smaller diameter than another end. A ring is slideable over the device to compress a wire that is within the channel.

In all embodiments, the wire torquing device can include a clip to secure coils of wire when not in use.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 illustrates a wire torquing device in accordance with one embodiment of the present invention.

FIG. 2 is a cross-sectional view of the wire torquing device shown in FIG. 1;

FIG. 3 illustrates a slider used within the wire torquing device shown in FIG. 1;

DETAILED DESCRIPTION OF THE PREFERRED EMBODIMENT

Figure 4:
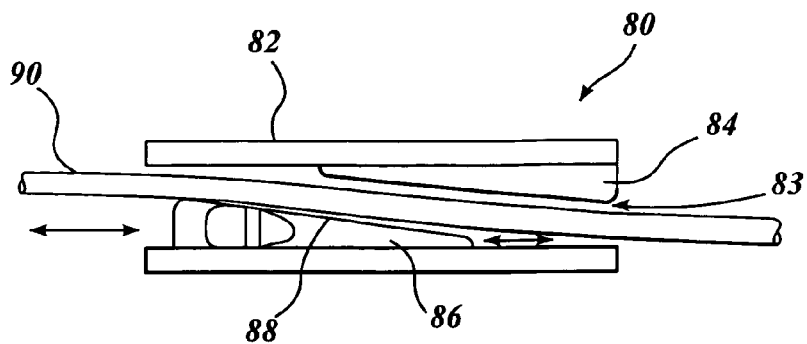
FIG. 4 illustrates a wire torquing device in accordance with another embodiment of the present invention.

As indicated above, the present invention is a device for applying torque to a thin wire or cable. Although the present invention is described with respect to applying torque to guidewires, those skilled in the art will recognize that the present invention can be used with any thin wire or cable that needs to be twisted.

FIG. 1 shows a side loading wire torquing device 20 in accordance with one exemplary embodiment of the present invention. The torquing device 20 includes a body portion 22 and a thumb actuated slider 24. The body portion 22 is formed as a U-shaped channel 26 having a tongue 28 that is suspended in the channel by a post 29. The tongue 28 is suspended vertically in the channel 26 by the post 29 such that a guidewire can fit underneath the tongue 28 and the bottom of the channel 26. The width of the channel 26 at its open end allows a guidewire to be laid alongside the tongue 28 and into the channel with one hand.

As best shown in FIG. 3, the slider 24 comprises a U- or other-shaped member having a center channel 30 and pair of thumb rests 32 formed at the free ends of the U-shaped member. The thumb rests 32 allow the user to move the slider 24 back and forth in the channel 26 of the body portion 22 with one hand. In order to secure the slider 24 in the body portion 22, the slider 24 has outwardly extending flanges 34 that fit within corresponding slots 36 that are formed in the interior of the side walls that define the channel 26 of the body portion 22.

The body portion 22 and the slider 24 of the wire torquing device 20 can be injection molded of a thermoplastic or other material. To assemble the torquing device 20, the slider 24 is snapped into the channel 26 of the body portion 22 such that the flanges 34 fit within the slots 36. A free end of the tongue 28 is suspended by the post 29 to extend into the center channel 30 of the slider 24 when the slider 24 is moved in the channel 26. The post 29 also engages one side of the slider 24 in order to limit the movement of the slider 24 in the channel 26. At the other end of the channel 26, the body portion 22 includes a pair of stops 38 that engage the thumb rests 32 to keep the slider 24 from sliding out of the device 20.

FIG. 2 illustrates how the slider 24 and the tongue 28 of the torquing device 20 engage a guidewire 50. First, the guidewire 50 is inserted into the center channel 30 of the slider 24 and the channel 26 of the body portion 22. A lower surface 42 of the tongue 28 is angled with respect to the bottom of the channel 26 so that one end of the tongue is closer to the bottom of the channel than the other end of the tongue. The bottom of the channel 30 has a similar cooperating angle. Urging the slider 24 towards the free end of the tongue 28 pinches the guidewire 50 between the bottom of the channel 30 in the slider and the lower surface 42 of the tongue 28, thereby gripping the guidewire. With the guidewire so secured, the physician can apply torque to the guidewire by rotating the torquing device 20.

The body portion 22 of the wire torquing device 20 may include a number of longitudinally extending ridges 46 or other recesses/protrusions on its outer surface that increase the grippability of the body portion 22. The guidewire torquing device 20 can be fitted over a guidewire and operated with one hand by a physician or their assistant. In order to remove the guidewire 50 from the torquing device 20, the physician or their assistant moves the slider 24 away from the free end of the tongue 28, thereby unpinching the guidewire. The guidewire can then be removed from the channel 30 in the slider 24 and the channel 26 of torquing device 20.

FIG. 4 illustrates another embodiment of a side loading wire torquing device 80 in accordance with the present invention. The torquing device 80 includes a body portion 82 having a center channel 83 and a wedge 84 secured to, or integrally formed with, an inner wall of the center channel 83 of the body portion 82. A movable slider 86 has a corresponding wedge shaped surface 88 such that a guidewire 90 placed in the channel 83 of the body portion 82 can be pinched against the wedge 84 by movement of the slider 86 against the wedge 84.

The engaging surfaces of the slider 86 and the wedge 84 may include a grip-enhancing device such as a ridged, roughened or rubberized surface, etc., to enhance the hold of the guidewire within the channel 83. Alternatively, the engaging surfaces of the wedge 84 and the slider 86 may be shaped to impart a bend in the guidewire as described below.

Figure 5A:
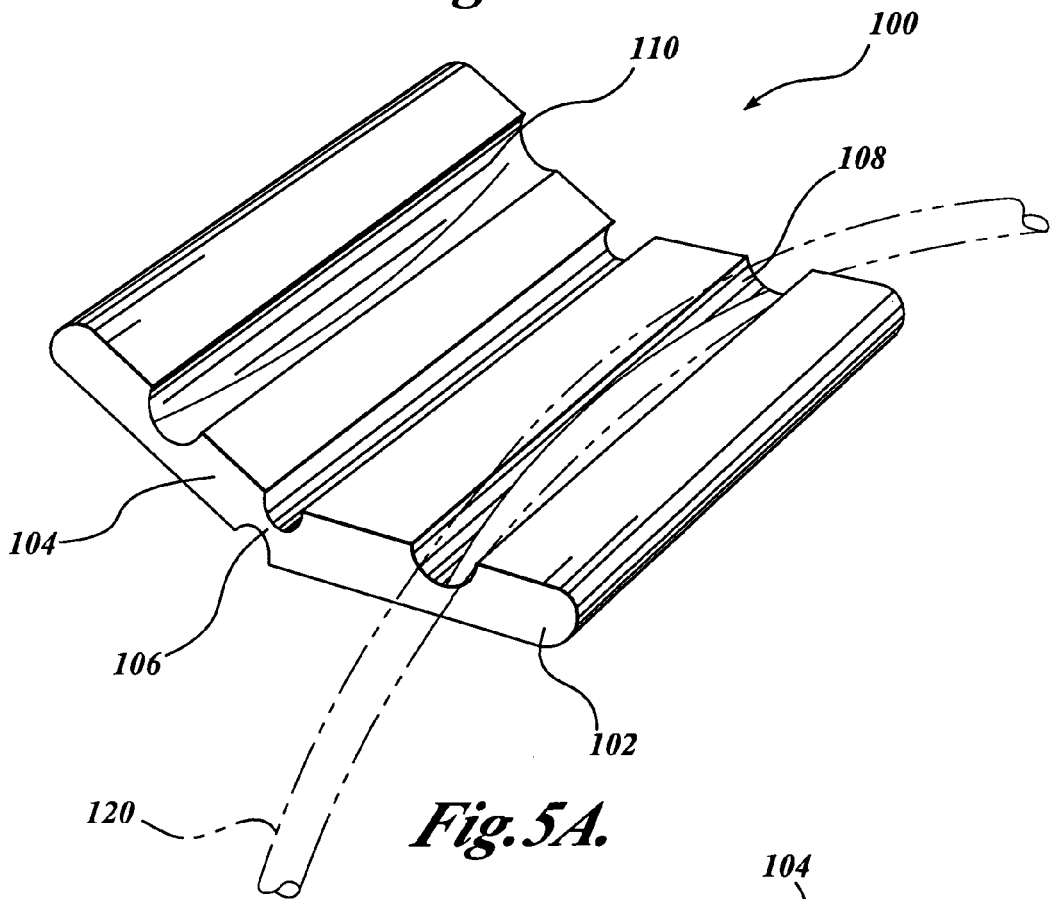
FIGS. 5A-5C illustrate a wire torquing device in accordance with yet another embodiment of the invention.

FIG. 5A illustrates a wire torquing device in accordance with an alternative embodiment of the present invention. The wire torquing device 100 has a clam shell structure with a lower section 102 and an upper section 104 that are joined by a hinge 106 that extends along the length of the joined upper and lower sections. The upper and lower sections 104, 102 are foldable over a guidewire 120 so that a physician can impart torque to the guidewire 120 by turning the torquing device 100. The guidewire 120 fits within a channel 108 in the lower section 102 and a corresponding channel 110 that is formed in the upper section 104. The two channels 108 and 110 align when the upper section 104 is closed on the lower section 102. Each of the channels 108 and 110 are formed such that a bend is imparted to the guidewire 120 when the upper section 104 is closed on the lower section 102. In one embodiment of the invention, the bend is achieved by forming an arcuate support in the channel 108 and a corresponding arcuate recess in the channel 110 or vice versa. The bend in the guidewire increases the torque that can be applied to the guidewire when the torquing device 100 is rotated.

To use the torquing device 100, the physician lays a guidewire 120 in the channel 108 and closes the upper section 104 over the lower section 102. The torquing device 100 may include a latch (not shown) or other locking mechanism that keeps the upper section 104 engaged with the lower section 102. With the torquing device secured around the guidewire, the physician can then turn the torquing device 100 to impart a torque to the guidewire 120.

Figure 5B:
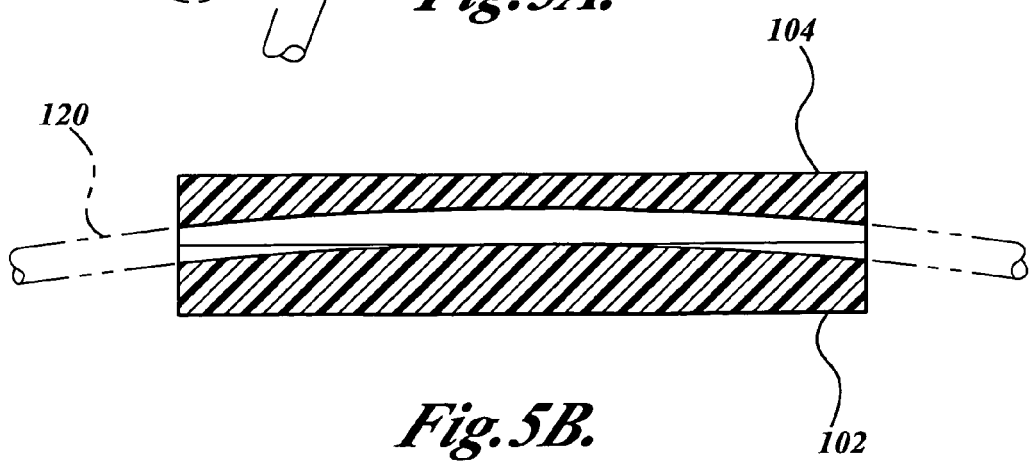
Figure 5C:
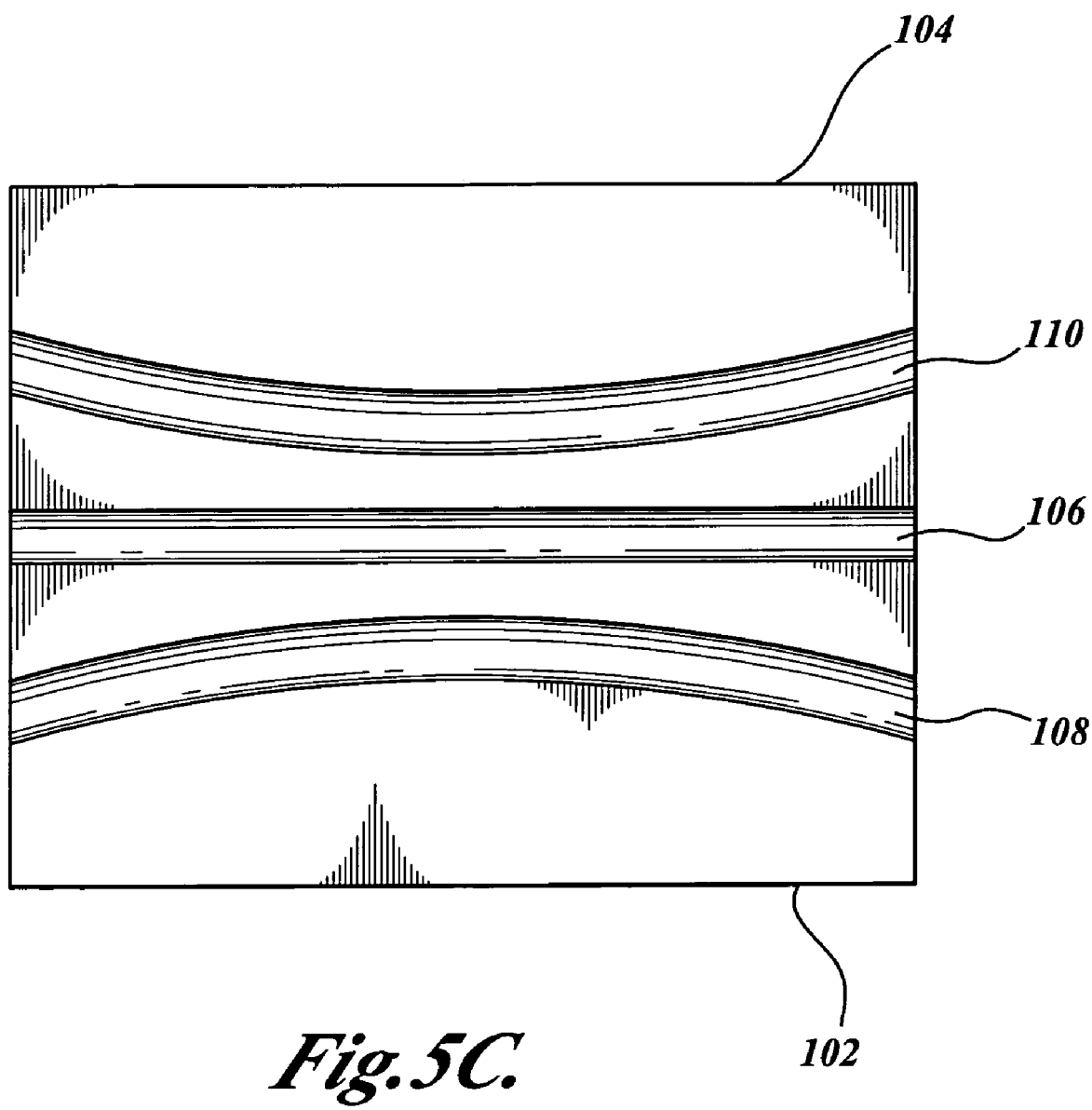

In the embodiment shown in FIGS. 5A and 5B, the bend in the guidewire 120 is oriented generally in a direction normal to the plane of the upper and lower sections 102 and 104. However, it will be appreciated that the channel 108 may be curved in the same plane of the sections 102 and 104 as shown in FIG. 5C. The sharper the bend that can be imparted to the guidewire 120, the greater the torque that is applied to the guidewire 120 as the torquing device 100 is rotated by a physician. The channels may be gently curved as shown in FIGS. 5A, 5B, and 5C, or may be more sharply curved or sinusoidal in shape.

Figure 6:
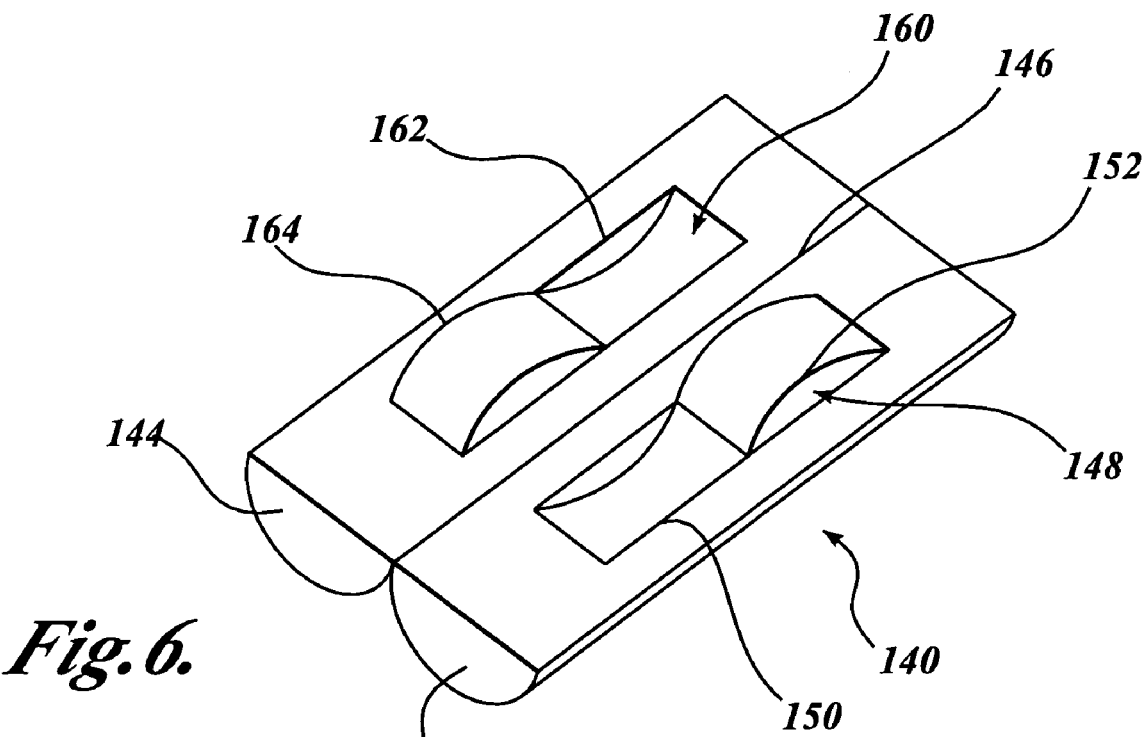
FIG. 6 illustrates a wire torquing device in accordance with yet another embodiment of the invention.

FIG. 6 shows an alternate embodiment of a wire torquing device 140, in accordance with another embodiment of the present invention. The wire torquing device 140 includes a bottom section 142 and a top section 144 that are joined by a hinge 146 that extends along a length of the joined edges. If desired, the free ends of the top and bottom sections may be held together with a latch or other locking mechanism (not shown).

Within the bottom section 142 is a channel 148 in which a guidewire is placed. The channel 148 has an arcuate recess 150 and an arcuate support 152, such that the path along the length of the channel 150 forms an S-shaped bend. A channel 160 in the upper section 144 has a cooperating arcuate recess 162 that aligns with the arcuate support 152 and an arcuate support 164 that aligns with the arcuate recess 150. When a guidewire is inserted into the channel 148 and the top section 144 is closed about the hinge 146, an S-shaped bend is created in the guidewire to increase the torque that can be applied to the guidewire. Although the channels shown have two bends, it would be appreciated that more bends could be placed in the channel if desired. The torquing device 140 can be molded from a thermoplastic or other material.

Figure 7:
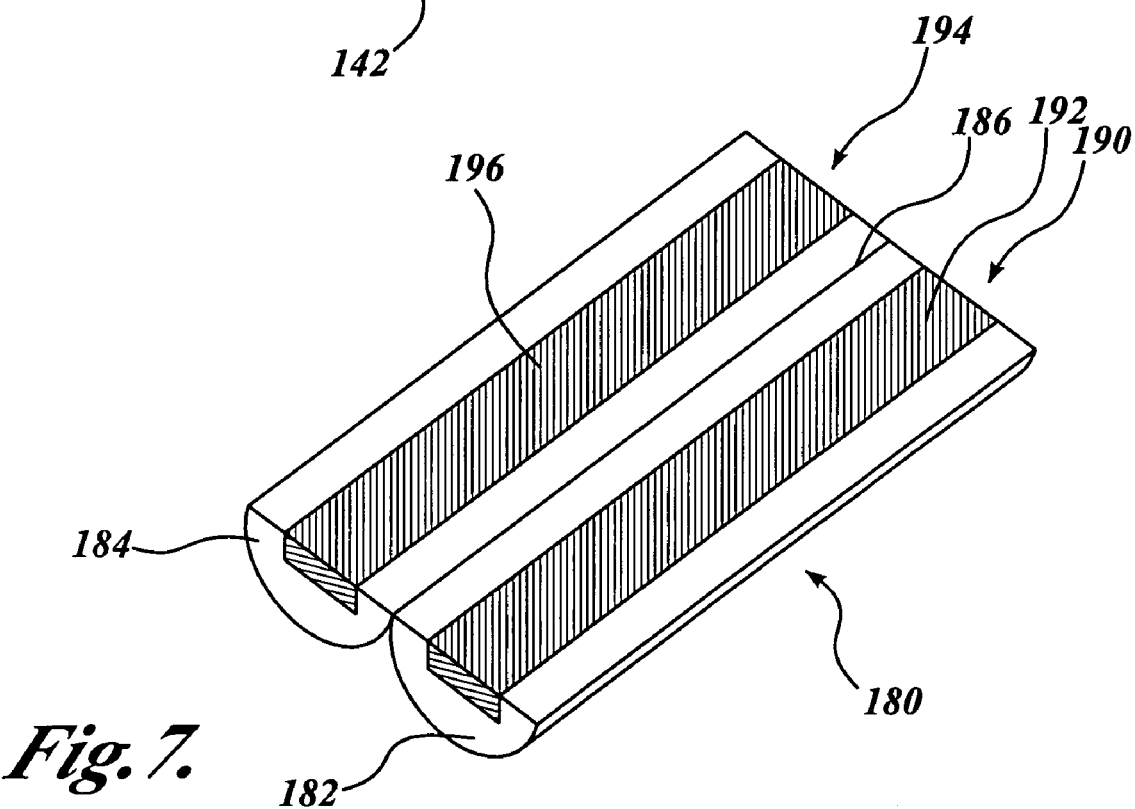
FIG. 7 illustrates a wire torquing device in accordance with yet another embodiment of the invention.

FIG. 7 illustrates another embodiment of a wire torquing device in accordance with the present invention. The wire torquing device 180 has a clam shell structure with a bottom section 182 and a top section 184 that are joined by hinge 186 that extends along a length of the joined sides of the bottom section and top section. As with the other embodiments, a latch or other locking device (not shown) may hold the free sides of the top and bottom sections together when closed about the hinge 186. The bottom section 182 includes a channel 190 extending along its length. Within the channel is a grip enhancing material 192 such as a latex strip, sandpaper, or other rubberized or grip enhancing material. Similarly, the top section 184 includes a channel 194 extending along its length. Within the channel 194 is a grip enhancing material 196 such as a latex, sandpaper, or other rubberized or grip enhancing material.

In use, a physician lays a guidewire (not shown) in the channel 190 and closes the top section 194 over the bottom section 182. The gripping material within the channels 190, 194 grips the guidewire such that as the physician rotates the torquing device 180, the torque is supplied to the distal end of the guidewire.

Figure 8A:
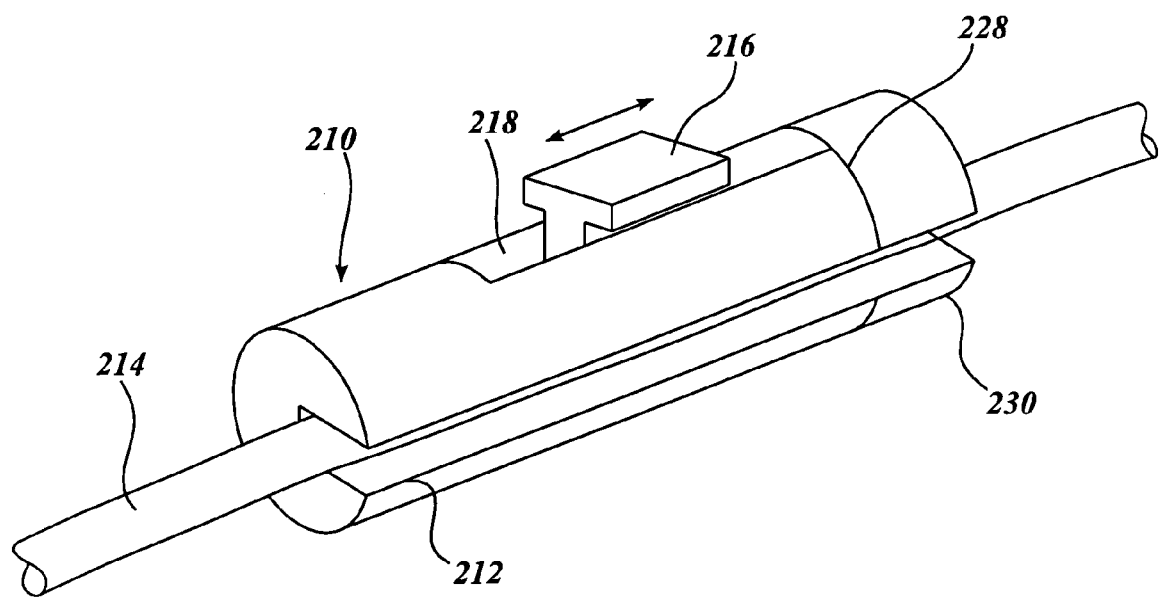
FIGS. 8A and 8B illustrate another embodiment of a wire torquing device in accordance with the present invention.
Figure 8B:
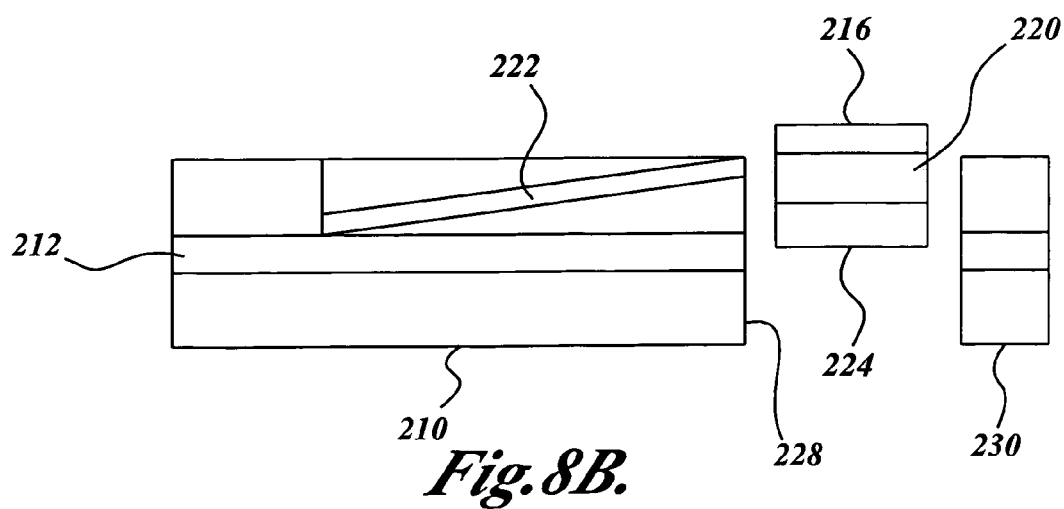

Yet another embodiment of a wire torquing device is shown in FIGS. 8A and 8B. In this embodiment, a wire torquing device 210 comprises a body portion having an open channel 212 extending along its length. A physician or their assistant can load a guidewire into the device by placing a guidewire 214 in the channel 212. The body also includes a slot 218 that is preferably oriented at 90° to the orientation of the channel 212. Within the slot 218 is a slider 216.

The slider 216 may comprise an I-beam- or other-shaped member having recesses 220 on either side that cooperate with protruding ribs 222 in the slot 218. The ribs 222 are preferably angled in the slot 218 such that movement of the slider 216 along the length of the slot 218 causes the bottom surface 224 of the slider 216 to be forced toward a wall of the channel 212.

When a guidewire is positioned in the channel 212, movement of the slider 216 in the channel pinches the guidewire between the bottom surface of the slider 216 and a wall of the channel 212.

To construct the guidewire torquing device 210, the slider 216 can be inserted into an open end 228 of the slot 218 and an endcap 230 secured over the end of the guidewire torquing device in order to close the slot 218. Although the slider 216 is shown as having an I-beam shape with recesses 220 that receive corresponding ribs 222, it will be appreciated that the slider 216 may include outwardly extending ribs that are received in corresponding angled slots in the guidewire torquing device or other cooperating mechanisms that force the bottom surface toward the center axis of the torquing device as it is moved in the slot 218. Similarly, it is also possible to construct the device 210 such that the channel 212 is angled with respect to the bottom surface of the slider instead of vice versa.

To use the guidewire torquing device 210, the physician or their assistant lays the guidewire 214 in the channel 212 and selectively moves the slider 216 in the slot 218 in order to pinch the guidewire such that rotation of the guidewire torquing device 210 imparts torque to the guidewire 214. Upon retraction of the slider 216, the guidewire is released and can be removed from the channel 212.

Figure 9:
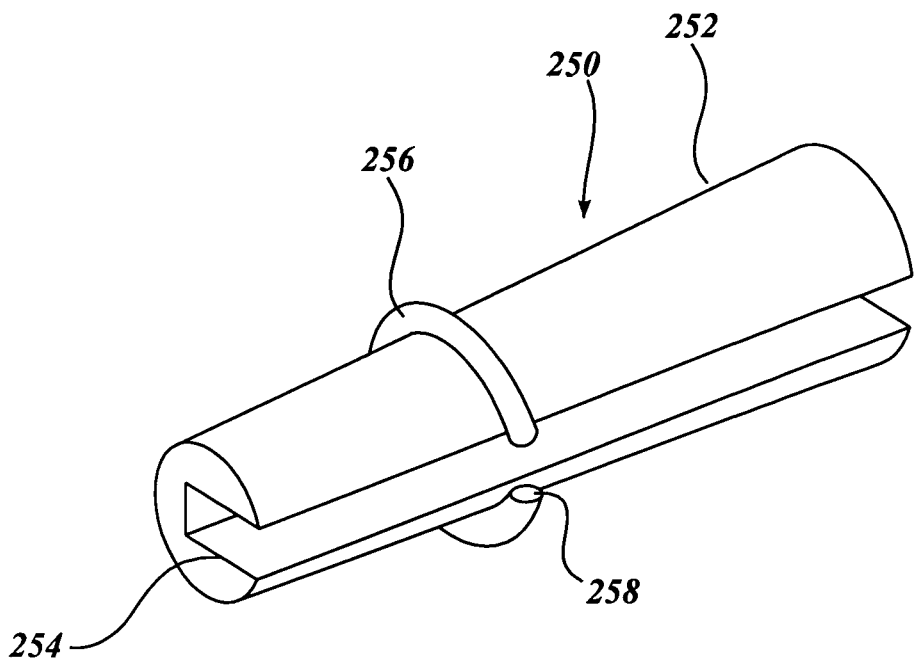
FIG. 9 illustrates yet another embodiment of a wire torquing device in accordance with the present invention.

FIG. 9 shows yet another alternative embodiment of a guidewire torquing device in accordance with the recent invention. In this embodiment, a wire torquing device 250 includes a tapered body 252. A channel 254 extends along the side of the body 252 such that a guidewire can be placed in the channel 254. A ring 256 is positioned over the torquing device 250 such that movement of the ring 256 causes the channel 254 to be compressed around a guidewire within the channel 254. The torquing device 250 is preferably made of a resilient plastic that is compressible by the ring 256. The ring 256 may include handles or grips to aid in pulling the ring along the length of the guidewire torquing device. In addition, the ring 256 may be rotated such that an opening 258 of the ring is not aligned with the opening in channel 254. With the opening in the ring 258 rotated, the channel 254 is closed and the guidewire is prevented from exiting the side of the wire torquing device 250.

The wire torquing device 250 is preferably made of a flexible plastic material such as polyethylene, polyurethane or other thermoplastic material that will plastically deform under the compression force exerted as the ring 256 is moved along its length. In addition, the material selected should allow the channel 254 to reopen once the ring 256 is moved toward the smaller end of the torquing device.

Figure 10:
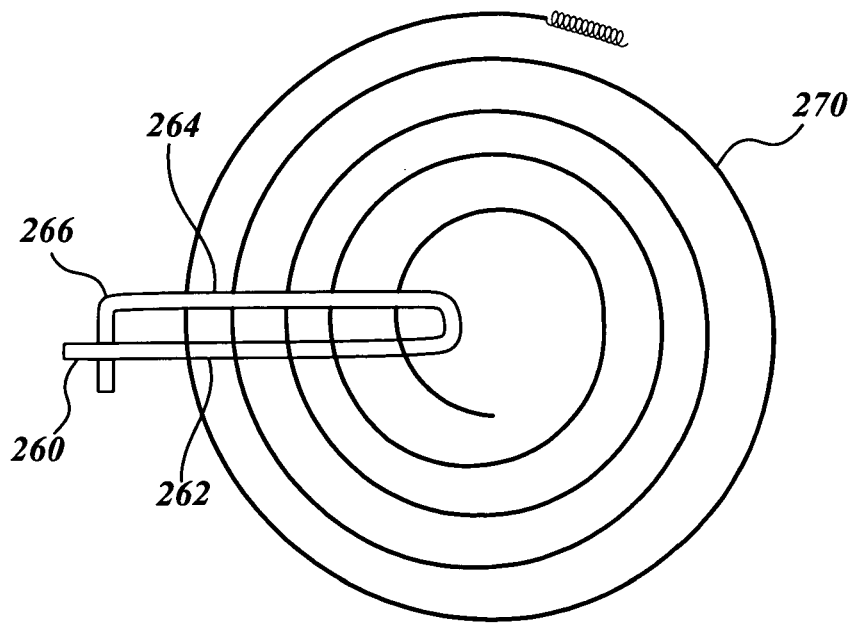
FIG. 10 illustrates a wire clip that can be used with the wire torquing devices of the present invention.

FIG. 10 shows an addition that can be combined with any of the guidewire torquing devices described above or used alone. The device comprises a guidewire retaining clip 260 that maintains a guidewire in a coil when not being used by a physician. The guidewire retaining clip 260 includes a pair of jaws 262, 264 folded back over each other and are secured together with a clip 266 at the end of the jaw. The jaws 262, 264 are placed around a number of wire coils 270 in order to maintain the coils 270 in a neat configuration when the wire is not being used. The clip 266 is then secured in order to lock the jaws 262, 264 together. The guidewire retaining clip 260 can be secured to or integrally formed with any of the wire torquing devices described above.

While the preferred embodiments of the invention have been illustrated and described, it will be appreciated that various changes can be made therein without departing from the scope of the invention. It is therefore intended that the scope of the invention be determined from the following claims and equivalents thereof.

The invention claimed is:

1. A device for applying torque to a wire, comprising:
   a body portion having an open ended channel with opposed side surfaces and a bottom surface that extend along an entire length of the body portion for allowing the wire to be side-loaded into the channel;
   a tongue that is separate from the body portion and fixedly suspended in the channel between the opposing side surfaces, the tongue including a first engagement surface positioned above the bottom surface of the channel and facing downwardly into the channel toward the bottom surface;
   a slider that is longitudinally slideable within the open ended channel of the body portion, the slider having a second engagement surface disposed adjacent the wire when the wire is side-loaded in the channel; and
   wherein longitudinal movement of the slider within the open ended channel of the body portion towards the tongue compresses the wire between the first, downwardly facing engagement surface of the fixed tongue and the second engagement surface of the slider so that rotation of the body portion applies torque to the wire.

2. The device of claim 1, wherein the first engagement surface of the tongue and the second engagement surface of the slider are angled in a similar manner with respect to the bottom surface of the open ended channel so that the wire is compressed therebetween.

3. The device of claim 1, wherein the body portion has a grip enhancing mechanism.

4. The device of claim 3, wherein the grip enhancing mechanism comprises one or more ridges on the exterior of the body portion.

5. The device of claim 1, wherein the tongue is defined by the body portion.

6. The device of claim 1, wherein the slider is U-shaped and includes an open ended channel, and wherein the second engagement surface of the U-shaped slider forms a portion of the open ended channel of the slider, the open ended channel of the U-shaped slider receiving the wire when the wire is side loaded in the channel of the body portion.

7. The device of claim 1, wherein the open ended channel of the body is U-shaped.

8. The device of claim 1, wherein the slider is capable of moving independently from the tongue.

9. A wire torquing device, comprising:
   a body having a length;
   an open ended channel having a bottom surface, the open ended channel extending along the entire length of the body into which a wire can be laterally fitted;

a projection that is separate from the body, projects into the open ended channels and is fixedly suspended above the bottom surface;

a slider that remains in the open ended channel as the wire is laterally fitted along the length of the open ended channel and is movable longitudinally therein, the slider including an open ended channel configured for laterally receiving the wire and being substantially aligned with the open ended channel of the body, the open ended channel of the slider defining an engagement surface; and wherein the open ended channel of the slider laterally receives a portion of the wire when laterally fitted in the open ended channel of the body, and wherein the engagement surface of the slider secures the portion of the wire against the fixed projection as the slider is moved longitudinally toward the projection in the open ended channel of the body.

10. The wire torquing device of claim 9, further comprising a tongue disposed in the open ended channel, wherein the tongue cooperates with the engagement surface on the slider to secure the wire in a fixed position.

11. A wire torquing device comprising:

a body having an open U-shaped channel extending along an entire length thereof in which a wire can be fitted, wherein the open U-shaped channel includes a pair of opposing side walls and a bottom surface;

a wedge fixedly positioned on one of the side walls of the U-shaped channel and having an angled engagement surface projecting laterally inwardly into the U-shaped channel;

a slider that is movable longitudinally within the channel;

wherein the slider includes a side engagement surface facing the angled engagement surface of the wedge; the slider being longitudinally movable towards the fixed wedge to pinch the wire between the side engagement surface of the slider and the angled engagement surface of the wedge.

* * * * *